US010488765B2

(12) United States Patent
Van Boxmeer et al.

(10) Patent No.: US 10,488,765 B2
(45) Date of Patent: Nov. 26, 2019

(54) METHOD OF OPTIMIZING THE POSITION AND/OR SIZE OF A MEASUREMENT ILLUMINATION SPOT RELATIVE TO A TARGET ON A SUBSTRATE, AND ASSOCIATED APPARATUS

(71) Applicant: ASML Netherlands B.V., Veldhoven (NL)

(72) Inventors: Johan Maria Van Boxmeer, Sint-Oedenrode (NL); Marinus Johannes Maria Van Dam, Venlo (NL); Koos Van Berkel, Waalre (NL); Sietse Thijmen Van Der Post, Utrecht (NL); Johannes Hubertus Antonius Van De Rijdt, Gemert (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/144,013

(22) Filed: Sep. 27, 2018

(65) Prior Publication Data

US 2019/0107786 A1 Apr. 11, 2019

(30) Foreign Application Priority Data

Oct. 11, 2017 (EP) ..................... 17195853

(51) Int. Cl.
*G03F 7/20* (2006.01)
*G01J 3/18* (2006.01)
(Continued)

(52) U.S. Cl.
CPC ............ *G03F 7/70641* (2013.01); *G01J 3/18* (2013.01); *G01N 21/4788* (2013.01);
(Continued)

(58) Field of Classification Search
CPC ............ G03F 7/70275; G03F 7/70641; G03F 7/70158; G03F 7/70625; G03F 7/70633
(Continued)

(56) References Cited

U.S. PATENT DOCUMENTS

2006/0033921 A1 2/2006 Den Boef et al.
2006/0066855 A1 3/2006 Boef et al.
(Continued)

FOREIGN PATENT DOCUMENTS

EP 1 930 774 A1 6/2008
WO WO 2012/126718 A1 9/2012
(Continued)

OTHER PUBLICATIONS

International Search Report and Written Opinion of the International Searching Authority directed to related International Patent Application No. PCT/EP2018/075380, dated Jan. 7, 2019; 12 pages.

*Primary Examiner* — Hung Nguyen
(74) *Attorney, Agent, or Firm* — Sterne, Kessler, Goldstein & Fox P.L.L.C.

(57) ABSTRACT

Disclosed is a method of optimizing within an inspection apparatus, the position and/or size (and therefore focus) of a measurement illumination spot relative to a target on a substrate. The method comprises detecting scattered radiation from at least the target resultant from illuminating the target, for different sizes and/or positions of said illumination spot relative to the target; and optimizing said position and/or size of the measurement illumination spot relative to the target based on a characteristic of the detected scattered radiation for the different sizes and/or positions of said illumination spot relative to the target.

13 Claims, 8 Drawing Sheets

(51) Int. Cl.
    *G01N 21/88*     (2006.01)
    *G01N 21/47*     (2006.01)

(52) U.S. Cl.
    CPC ....... *G01N 21/8806* (2013.01); *G03F 7/7065* (2013.01); *G03F 7/70158* (2013.01); *G03F 7/70616* (2013.01); *G03F 7/70625* (2013.01); *G03F 7/70633* (2013.01)

(58) Field of Classification Search
    USPC .......................................... 355/52, 53, 55, 67
    See application file for complete search history.

(56) References Cited

U.S. PATENT DOCUMENTS

| | | | |
|---|---|---|---|
| 2007/0002301 A1* | 1/2007 | Venema | G03F 7/70275 |
| | | | 355/69 |
| 2008/0151228 A1 | 6/2008 | Hugers | |
| 2009/0040525 A1* | 2/2009 | Kadkly | G01N 21/9501 |
| | | | 356/446 |
| 2010/0201963 A1 | 8/2010 | Cramer et al. | |
| 2010/0230580 A1* | 9/2010 | Matsumoto | G02B 7/28 |
| | | | 250/208.1 |
| 2010/0328655 A1 | 12/2010 | Den Boef | |
| 2011/0027704 A1 | 2/2011 | Cramer et al. | |
| 2011/0043791 A1 | 2/2011 | Smilde et al. | |
| 2011/0069292 A1 | 3/2011 | Den Boef | |
| 2012/0044470 A1 | 2/2012 | Smilde et al. | |
| 2012/0123581 A1 | 5/2012 | Smilde et al. | |
| 2013/0258310 A1 | 10/2013 | Smilde et al. | |
| 2013/0271740 A1 | 10/2013 | Quintanilha | |
| 2014/0139814 A1 | 5/2014 | Cramer et al. | |
| 2018/0061691 A1* | 3/2018 | Jain | H01L 22/12 |

FOREIGN PATENT DOCUMENTS

| | | |
|---|---|---|
| WO | WO 2013/178422 A1 | 12/2013 |
| WO | WO 2014/082938 A1 | 6/2014 |
| WO | WO 2016/133765 A1 | 8/2016 |
| WO | WO 2017/055072 A1 | 4/2017 |

* cited by examiner

METHOD OF OPTIMIZING THE POSITION AND/OR SIZE OF A MEASUREMENT ILLUMINATION SPOT RELATIVE TO A TARGET ON A SUBSTRATE, AND ASSOCIATED APPARATUS

FIELD

The present invention relates to a method for monitoring a characteristic of illumination from a metrology apparatus. The invention may be applied for example in an inspection apparatus.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 2012126718. Methods and scatterometers are also disclosed in US20110027704A1, US2006033921A1 and US2010201963A1. In addition to scatterometry to determine parameters of a structure made in one patterning step, the methods and apparatus can be applied to perform diffraction-based overlay measurements. Diffraction-based overlay metrology using dark-field image detection of the diffraction orders enables overlay measurements on smaller targets. Examples of dark-field imaging metrology can be found in international patent applications US2010328655 A1 and US2011069292 A1. Further developments of the technique have been described in published patent applications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference. The invention is not limited in application to any particular type of inspection apparatus, or even to inspection apparatuses generally.

A common problem in inspection apparatuses is one of controlling focusing of the optical system onto a target. Many systems require control of focus of the optical system within very tight tolerances. A focus control arrangement for a scatterometer of the type described above is disclosed for example in published patent application US20080151228A. Light reflected from the target is imaged with deliberate focus error on two photodetectors. Comparing the light intensity between the two photodetectors allows an indication of defocus to be obtained, and the direction of defocus to be identified. The contents of that application are incorporated herein by reference.

Another problem in inspection apparatuses is one of aligning the illumination spot onto a target. This is particularly an issue with soft X-ray or EUV measurement radiation as such systems typically have a long optical path and reflective optics leading to drifts and pointing errors over the optical path. Another known alignment issue relates to inspection apparatuses suitable for measuring in-device targets (targets surrounded by device structures rather than in the scribe lane). For metrology on such in-device targets, which may use visible wavelengths, the illumination spot is also underfilled, and therefore alignment is difficult due to the surrounding product structures.

It is desirable to improve accuracy of monitoring a characteristic of illumination from a metrology apparatus. For example, it is desirable to improve the focus accuracy and/or alignment accuracy that can be achieved.

SUMMARY

According to the present invention in a first aspect, there is disclosed a method of optimizing within an inspection apparatus, the position and/or size of a measurement illumination spot relative to a target on a substrate, said method comprising: detecting scattered radiation from at least the target resultant from illuminating the target, for different sizes and/or positions of said illumination spot relative to the target: and optimizing said position and/or size of the measurement illumination spot relative to the target based on a characteristic of the detected scattered radiation for the different sizes and/or positions of said illumination spot relative to the target.

Other aspects of the invention include a metrology apparatus for measuring a parameter of a lithographic process, the metrology apparatus being operable to perform the method of the first aspect, and a non-transitory computer program product comprising machine-readable instructions for causing a processor to cause performance of the method of the first aspect.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Figure 1:
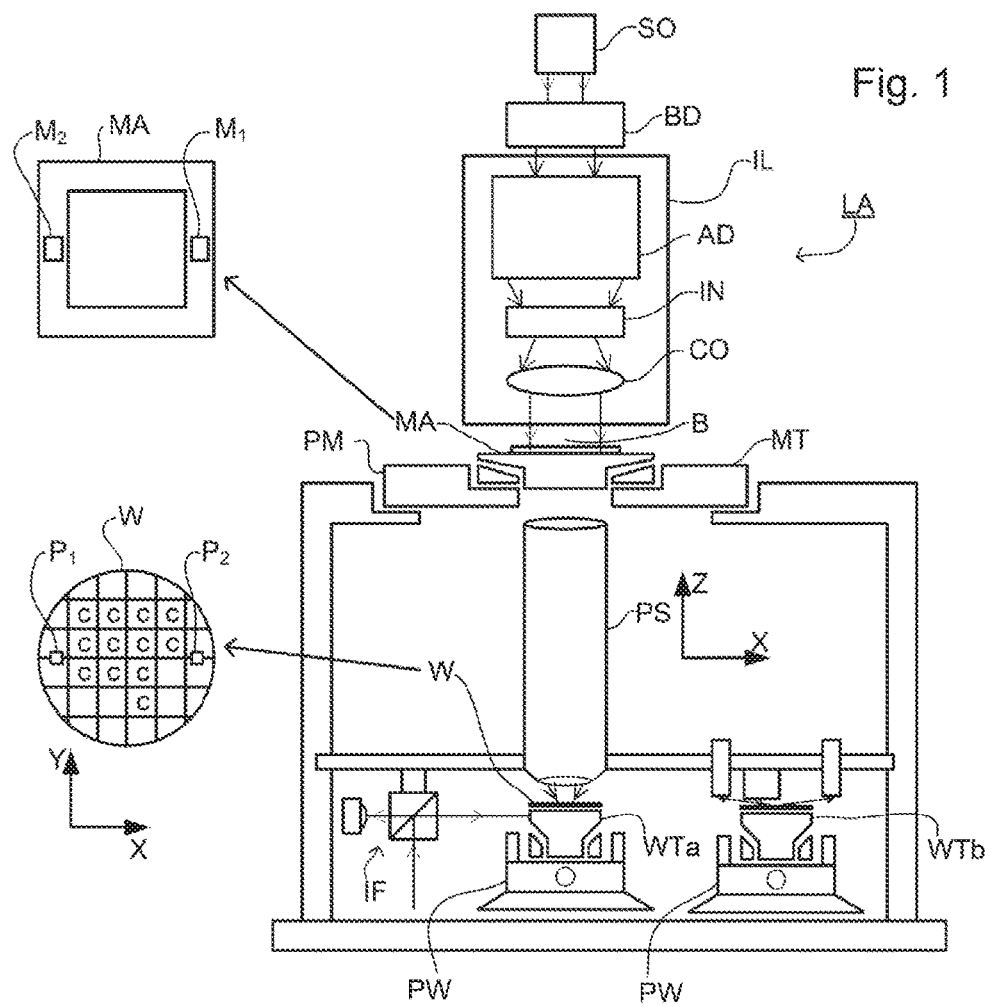
FIG. 1 depicts a lithographic apparatus.

FIG. 1 schematically depicts a lithographic apparatus LA. The lithographic apparatus LA comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device MA in accordance with certain parameters;
- a substrate table (e.g. a wafer table) WT constructed to hold a substrate (e.g. a resist-coated wafer) W and connected to a second positioner PW configured to accurately position the substrate W in accordance with certain parameters, and
- a projection system (e.g. a refractive projection lens system) PS configured to project a pattern imparted to the radiation beam B by patterning device MA onto a target portion C (e.g. comprising one or more dies) of the substrate W.

The illumination system IL may include various types of optical components, such as refractive, reflective, magnetic, electromagnetic, electrostatic or other types of optical components, or any combination thereof, for directing, shaping, or controlling radiation.

The support structure MT supports, i.e. bears the weight of, the patterning device MA. It holds the patterning device MA in a manner that depends on the orientation of the patterning device MA, the design of the lithographic apparatus LA, and other conditions, such as for example whether or not the patterning device MA is held in a vacuum environment. The support structure MT can use mechanical, vacuum, electrostatic or other clamping techniques to hold the patterning device MA. The support structure MT may be a frame or a table, for example, which may be fixed or movable as required. The support structure MT may ensure that the patterning device MA is at a desired position, for example with respect to the projection system PS. Any use of the terms "reticle" or "mask" herein may be considered synonymous with the more general term "patterning device."

The term "patterning device" used herein should be broadly interpreted as referring to any device that can be used to impart a radiation beam B with a pattern in its cross-section such as to create a pattern in a target portion C of the substrate W. It should be noted that the pattern imparted to the radiation beam B may not exactly correspond to the desired pattern in the target portion C of the substrate W, for example if the pattern includes phase-shifting features or so called assist features. Generally, the pattern imparted to the radiation beam B will correspond to a particular functional layer in a device being created in the target portion C, such as an integrated circuit.

The patterning device MA may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the lithographic apparatus LA is of a transmissive type (e.g. employing a transmissive mask). Alternatively, the lithographic apparatus LA may be of a reflective type (e.g. employing a programmable mirror array of a type as referred to above, or employing a reflective mask).

The lithographic apparatus LA may be of a type having two (dual stage) or more substrate tables WTa, WTb (and/or two or more mask tables). In such "multiple stage" machines the additional tables may be used in parallel, or preparatory steps may be carried out on one or more tables while one or more other tables are being used for exposure.

The lithographic apparatus LA may also be of a type wherein at least a portion of the substrate W may be covered by a liquid having a relatively high refractive index, e.g. water, so as to fill a space between the projection system PS and the substrate W. An immersion liquid may also be applied to other spaces in the lithographic apparatus LA, for example, between the patterning device MA and the projection system PS. Immersion techniques are well known in the art for increasing the numerical aperture of the projection system PS. The term "immersion" as used herein does not mean that a structure, such as a substrate W, must be submerged in liquid, but rather only means that liquid is located between the projection system PS and the substrate W during exposure.

Referring to FIG. 1, the illumination system IL receives a radiation beam B from a radiation source SO. The radiation source SO and the lithographic apparatus LA may be separate entities, for example when the radiation source SO is an excimer laser. In such cases, the radiation source SO is not considered to form part of the lithographic apparatus LA and the radiation beam B is passed from the radiation source SO to the illumination system IL with the aid of a beam delivery system BD comprising, for example, suitable directing mirrors and/or a beam expander. In other cases the radiation source SO may be an integral part of the lithographic apparatus LA, for example when the radiation source SO is a mercury lamp. The radiation source SO and the illumination system IL, together with the beam delivery system BD if required, may be referred to as a radiation system.

The illumination system IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illumination system IL can be adjusted. In addition, the illumination system IL may comprise various other components, such as an integrator IN and a condenser CO. The illumination system IL may be used to condition the radiation beam B, to have a desired uniformity and intensity distribution in its cross-section.

The radiation beam B is incident on the patterning device (e.g., mask) MA, which is held on the support structure (e.g., mask table) MT, and is patterned by the patterning device MA. Having traversed the patterning device MA, the radiation beam B passes through the projection system PS, which focuses the radiation beam B onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using mask alignment marks $M_1$, $M_2$ and substrate alignment marks $P_1$, $P_2$. Although the substrate alignment marks $P_1$, $P_2$ as illustrated occupy dedicated target portions C, they may be located in spaces between target portions C (these are known as scribe-lane alignment marks). Similarly, in situations in which more than one die is provided on the patterning device MA, the mask alignment marks $M_1$, $M_2$ may be located between the dies.

The depicted lithographic apparatus LA could be used in at least one of the following modes:

1. In step mode, the support structure MT and the substrate table WT are kept essentially stationary, while an entire pattern imparted to the radiation beam B is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam B is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion C in a single dynamic exposure, whereas the length of the scanning motion determines the height (in the scanning direction) of the target portion C.

3. In another mode, the support structure MT is kept essentially stationary holding a programmable patterning device MA, and the substrate table WT is moved or scanned while a pattern imparted to the radiation beam B is projected onto a target portion C. In this mode, generally a pulsed radiation source SO is employed and the programmable patterning device MA is updated as required after each movement of the substrate table WT or in between successive radiation pulses during a scan. This mode of operation can be readily applied to maskless lithography that utilizes programmable patterning device MA, such as a programmable mirror array of a type as referred to above.

Combinations and/or variations on the above described modes of use or entirely different modes of use may also be employed.

Figure 2:
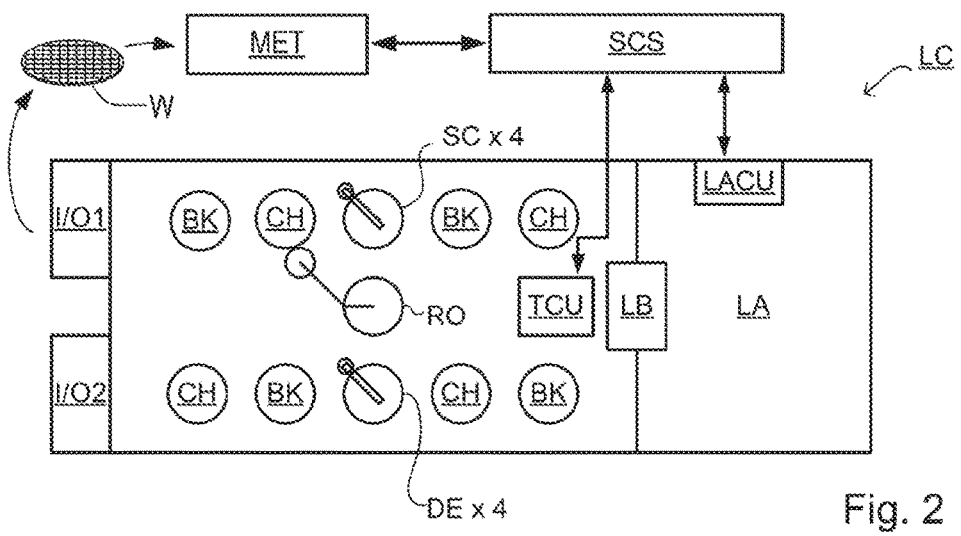
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates W from input/output ports I/O1, IO2, moves them between the different process apparatus and delivers then to the loading bay LB of the lithographic apparatus LA. These devices, which are often collectively referred to as the track, are under the control of a track control unit TCU which is itself controlled by the supervisory control system SCS, which also controls the lithographic apparatus LA via lithography control unit LACU. Thus, the different apparatus can be operated to maximize throughput and processing efficiency.

In order that the substrates W that are exposed by the lithographic apparatus LA are exposed correctly and consistently, it is desirable to inspect exposed substrates W to measure properties such as overlay errors between subsequent layers, line thicknesses, critical dimensions (CD), etc. Accordingly a manufacturing facility in which lithographic cell LC is located also includes metrology system MET which receives some or all of the substrates W that have been processed in the lithographic cell LC. Metrology results are provided directly or indirectly to the supervisory control system SCS. If errors are detected, adjustments may be made to exposures of subsequent substrates W, especially if the inspection can be done soon and fast enough that other substrates W of the same batch are still to be exposed. Also, already exposed substrates W may be stripped and reworked to improve yield, or discarded, thereby avoiding performing further processing on substrates W that are known to be faulty. In a case where only some target portions C of a substrate W are faulty, further exposures can be performed only on those target portions C which are good.

Within metrology system MET, an inspection apparatus is used to determine the properties of the substrates W, and in particular, how the properties of different substrates W or different layers of the same substrate W vary from layer to layer. The inspection apparatus may be integrated into the lithographic apparatus LA or the lithographic cell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates W and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
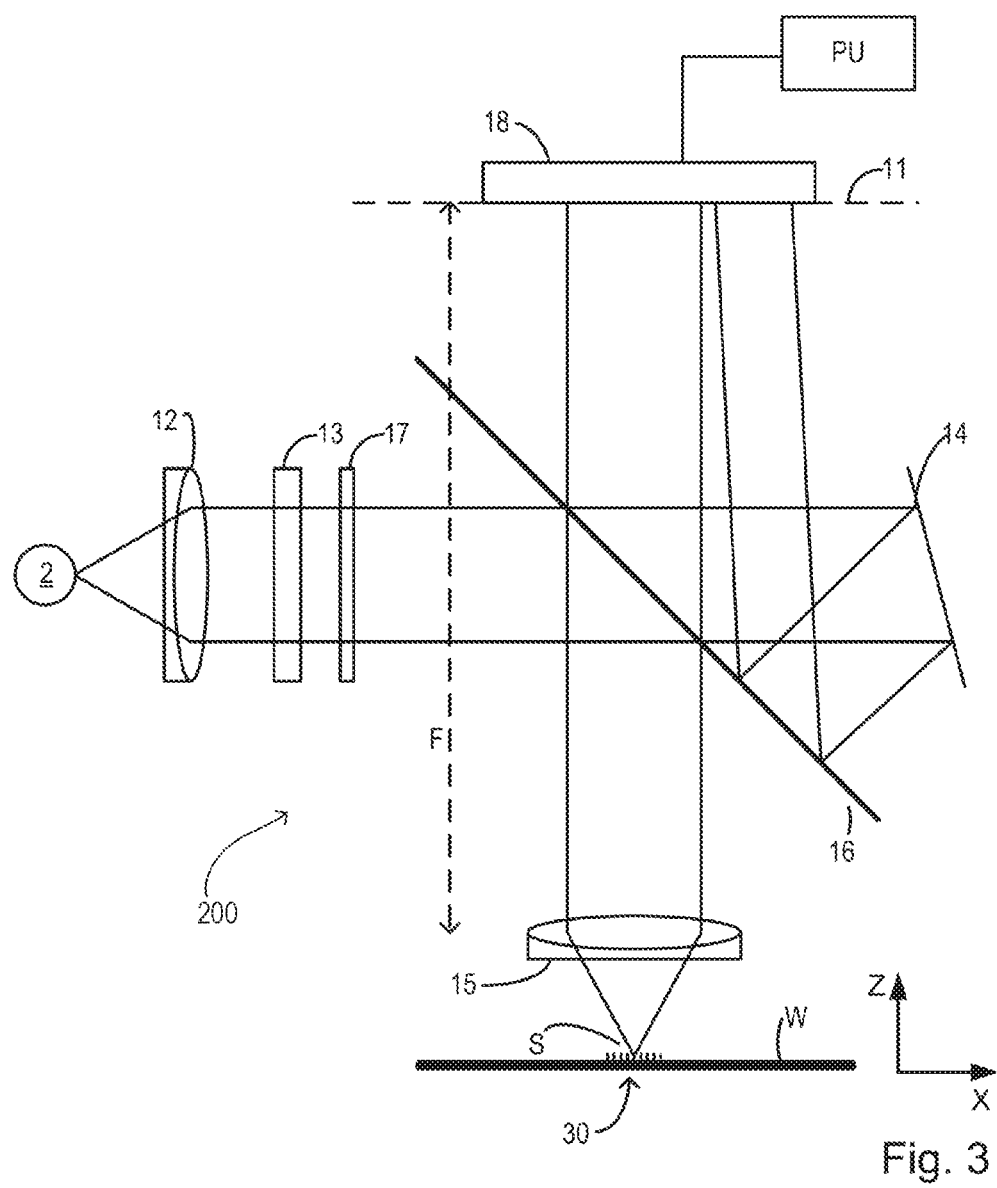
FIG. 3 depicts a known inspection apparatus arranged to perform angle-resolved scatterometry, as an example of an optical system in which a focus monitoring arrangement according to the present invention may be applied.

FIG. 3 depicts a known scatterometer 200. In this device, the radiation emitted by illumination source 2 is collimated using lens system 12 and transmitted through interference filter 13 and polarizer 17, reflected by partially reflecting surface 16 and is focused into a spot S on substrate W via a microscope objective lens 15, which has a high numerical aperture (NA), preferably at least 0.9 and more preferably at least 0.95. Immersion scatterometers may even have lenses with numerical apertures over 1.

As in the lithographic apparatus LA, one or more substrate tables WT may be provided to hold the substrate W during measurement operations. The substrate tables WT may be similar or identical in form to the substrate tables WTa, WTb of FIG. 1. In an example where the inspection apparatus is integrated with the lithographic apparatus LA, they may even be the same substrate tables WT. Coarse and fine positioners may be provided to a second positioner PW configured to accurately position the substrate W in relation to a measurement optical system. Various sensors and actuators are provided for example to acquire the position of a target of interest, and to bring it into position under the objective lens 16. Typically many measurements will be made on targets at different locations across substrate W. The substrate table WT can be moved in X and Y directions to acquire different targets, and in the Z direction to obtain a desired focusing of the optical system on the target. It is convenient to think and describe operations as if the objective lens 15 and optical system being brought to different locations on the substrate W, when in practice the optical system remains substantially stationary and only the substrate W moves. Provided the relative position of the substrate W and the optical system is correct, it does not matter in principle which one of those is moving in the real world, or if both are moving.

The reflected radiation then passes through partially reflecting surface 16 into a detector 18 in order to have the scatter spectrum detected. The detector 18 may be located in the back-projected pupil plane 11, which is at the focal length of the objective lens 15, however the pupil plane may instead be re-imaged with auxiliary optics (not shown) onto the detector 18. The pupil plane is the plane in which the radial position of radiation defines the angle of incidence and the angular position defines azimuth angle of the radiation. The detector 18 is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-200 nm. The interference filter 13 may be tunable rather than comprising a set of different filters. A grating could be used instead of interference filters 13. An aperture stop or spatial light modulator (not shown) may be provided in the illumination path to control the range of angle of incidence of radiation on the target.

The detector 18 may measure the intensity of scattered light at a single wavelength (or narrow wavelength range), the intensity separately at multiple wavelengths or integrated over a wavelength range. Furthermore, the detector 18 may separately measure the intensity of transverse magnetic- and transverse electric-polarized light and/or the phase difference between the transverse magnetic- and transverse electric-polarized light.

The substrate target 30 on substrate W may be a 1-D grating, which is printed such that after development, the bars are formed of solid resist lines. The substrate target 30 may be a 2-D grating, which is printed such that after development, the grating is formed of solid resist pillars or vias in the resist. The bars, pillars or vias may alternatively be etched into the substrate W. This pattern is sensitive to chromatic aberrations in the lithographic apparatus LA, particularly the projection system PS, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processor PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the substrate target 30 comprises one set of periodic features superimposed on another. The concepts of asymmetry measurement using the instrument of for instance FIG. 3 are described for example in published patent application US2006066855A1. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 3, where detector 18 may be an image sensor, such asymmetry in the diffraction orders appears directly as asymmetry in the pupil image recorded by detector 18. This asymmetry can be measured by digital image processing in processor PU, and calibrated against known values of overlay.

Figure 4:
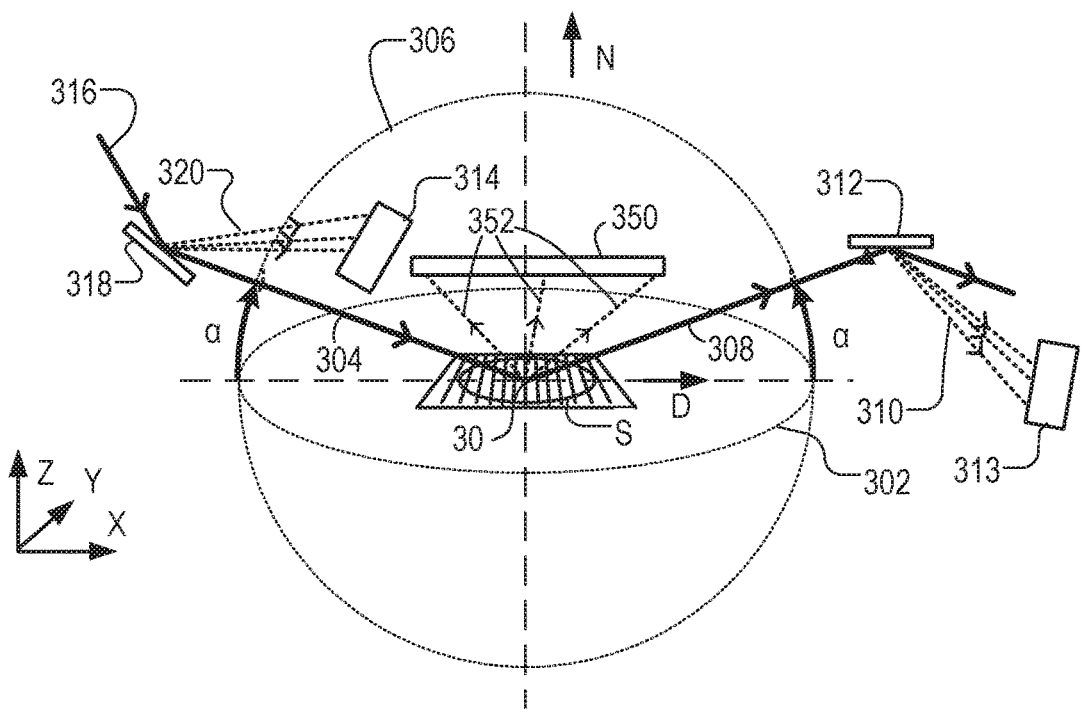
FIG. 4 schematically depicts a metrology method using EUV radiation.
Figure 5:
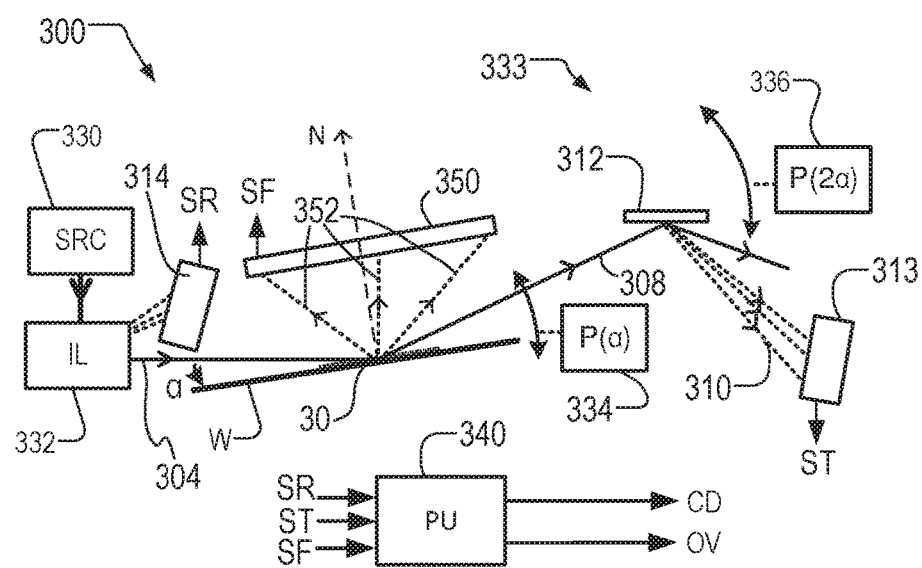
FIG. 5 schematically depicts an EUV metrology device according to an embodiment of the invention.

FIG. 4 illustrates an EUV metrology method while FIG. 5 illustrates an EUV metrology apparatus 300, which is an alternative apparatus to the metrology apparatus 200 of FIG. 3. The apparatus can be used as an example of EUV metrology apparatus for measuring parameters of substrates W processed in the manufacturing system of FIG. 1. The measurement radiation used by EUV metrology apparatus may comprise radiation in the wavelength range from 0.1 to 100 nm, or, optionally, in the wavelength range from 1 to 100 nm or, optionally, in the wavelength range from 1 to 50 nm, or optionally, in the wavelength range from 10 to 20 nm. Advantages of using such EUV radiation is that it can penetrate (and therefore measure) layers of certain materials that are opaque at other wavelengths. Another advantage of reducing the wavelength of the measurement radiation is that it makes resolution of smaller structures possible, thereby increasing sensitivity to structural variations of the structures. However, as EUV radiation is absorbed by transmissive optics, reflective optics are used to transport the measurement radiation to and from the substrate.

In FIG. 4, the target 30 is represented schematically as comprising a one-dimensional grating structure at the origin of a spherical reference frame. Axes X, Y and Z are defined relative to the target. (Of course any arbitrary coordinate system can be defined in principle, and each component may have its own local reference frame, that can be defined relative to the one shown.) The direction of periodicity D of the target structure is aligned with the X axis. The drawing is not a true perspective drawing, but a schematic illustration only. The X-Y plane is the plane of the target and substrate, and for clarity is shown tilted toward the viewer, represented by an oblique view of circle 302. The Z direction defines the direction N normal to the substrate. In FIG. 4, one of the incident rays is labeled 304 and has an angle $\alpha$ of grazing incidence. In this example, the incident ray 304 (and all incident rays forming the radiation spot S) lie substantially in a plane parallel to the X-Z plane, that is a plane defined the directions D and N and represented by circle 306. A reflected ray 308 that is not scattered by the periodic structure of the target 30 emerges towards the right hand side of the target in the diagram, with an elevation angle $\alpha$.

To perform spectroscopic reflectometry, ray 308 and other reflected rays are broken into a spectrum 310, comprising rays of different wavelengths. The spectrum may be produced for example using a grazing incidence diffraction grating 312. The spectrum is detected by a spectrum detector 313. This spectrum detector 313, which may for example be a CCD image detector having an array of pixels, is used to transform the spectrum into electrical signals and eventually digital data for analysis.

In addition to spectrum 310, higher (non-zero) diffraction orders 352 (e.g., at least the +1 and −1 orders, and possibly other higher orders) may be detected using a diffraction order detector 350. While one diffraction order detector 350 is shown here, more than one higher order detector may be used; for example, a first higher order detector for the +1 order, and a second higher order detector for the −1 order. Diffraction order detector 350 may for example be a CCD image detector having an array of pixels.

In a practical system, the spectrum of radiation 304 may be subject to time variations, which would disturb the analysis. In order to normalize the detected spectrum 310 and/or higher diffraction orders 352 against these variations, a reference spectrum is captured by a reference spectrum detector 314. To produce the reference spectrum, source radiation 316 is diffracted by another diffraction grating 318. A zero order reflected ray of grating 318 forms the incident ray 304, while the first order diffracted rays 320 of grating 318 form the reference spectrum detected by reference spectrum detector 314. Electrical signals and data representing the reference spectrum are obtained for use in the analysis.

From the measured spectrum 310 and/or higher diffraction orders 352, obtained for one or more values of incidence angle $\alpha$, a measurement of a property of the target structure T can be calculated in a manner described further below.

Turning to FIG. 5, EUV metrology apparatus 300 is provided for measuring properties of a metrology target 30 formed on substrate W, by the method of FIG. 4. Various hardware components are represented schematically. The practical implementation of these components can be performed by the relevant skilled persons applying a mixture of existing components and specially-designed components, according to well-known design principles. A support (not shown in detail) is provided for holding the substrate at a desired position and orientation relative to other components to be described. A radiation source 330 provides radiation to an illumination system 332. Illumination system 332 provides a beam of EUV measurement radiation represented by ray 304 which forms a focused irradiation spot on target 30. Illumination system 332 also provides the reference spectrum 320 to reference spectrum detector 314. Components 312, 313 etc. may be conveniently considered as a spectrum detection system 333.

Substrate W in this example is mounted on a movable support having a positioning system 334 such that an angle of incidence a of ray 304 can be adjusted and/or the x, y, z position of the substrate W can be adjusted. In this example, it is chosen as a matter of convenience to tilt the substrate W to change the incidence angle, while the source 330 and illumination system 332 remain stationary. In order to catch the reflected ray 308, detection system 333 is provided with a further movable support 336, so that it moves through an angle 2$a$ relative to the stationary illumination system, or through an angle $\alpha$ relative to the substrate. In the grazing incidence regime of reflectometry, it is convenient to define the incidence angle $\alpha$ by reference to the plane of the substrate, as shown. Of course, it could equally be defined as an angle between the direction of incidence of incident ray I and a direction N normal to the substrate.

Additional actuators, not shown, are provided for bringing each target 30 into a position where the focused spot S of radiation is located. (Looking at it another way, to bring the spot to the position where the target is located.) In a practical application, there may be a succession of individual targets or target locations to be measured on a single substrate, and a succession of substrates too. It is immaterial, in principle, whether the substrate and target are moved and reoriented while the illumination system and detectors 313, 350 stay still, or whether the substrate stays still while the illumination system and detectors 313, 350 are moved, or whether different components of the relative movement are achieved by a combination of these techniques. The present disclosure encompasses all these variants.

As already described with reference to FIG. 4, the radiation reflected by target 30 and substrate W is split into a spectrum 310 of rays of different wavelengths, before it impinges on spectrum detector 313. Spectrum detector 313 and/or diffraction order detector 350 comprises for example a position-sensitive EUV detector, typically an array of detector elements. In each case, the array may be a linear array, but in practice a 2-dimensional array of elements (pixels) may be provided. Spectrum detector 313 and/or diffraction order detector 350 may be for example a CCD (charge coupled device) image sensor.

A processor 340 receives signals from the detectors 350, 313 and 314. In particular, signal ST from spectrum detector 313 represents the target spectrum, signals SF from diffraction order detector 350 represents the higher order diffraction patterns and signal SR from detector 314 represents the reference spectrum. Processor 340 can subtract the reference spectrum from the target spectrum to obtain a reflection spectrum of the target, normalized against variation in the source spectrum. The resulting reflection spectra for one or more angles of incidence are used in the processor to calculate a measurement of property of the target, for example CD or overlay. Similarly, Processor 340 can subtract the reference spectrum from the higher diffraction order patterns (spectra) 352 to obtain higher order diffraction patterns which are normalized against variation in the source spectrum. These higher diffraction order patterns 352 can be compared in intensity asymmetry measurements to calculate a measurement of property of the target, for example overlay or focus.

In practice, radiation from source 330 may be provided in a series of short pulses and signals SR and ST may be captured together for each pulse. Difference signals for each individual pulse are calculated, before being aggregated into an overall reflection spectrum for this target at this angle of incidence. In this way, instability of the source spectrum between pulses is corrected for. The pulse rate may be thousands, or even tens of millions per second (hertz). The number of pulses aggregated to measure one reflection spectrum may be tens or thousands, for example. Even with so many pulses, the physical measurement takes a fraction of one second.

Applying this EUV spectroscopic reflectometry to metrology in semiconductor manufacturing, small grating metrology targets can be used. Multiple diffraction spectra are captured using detectors 350, 313 and 314, while setting the grazing angle of incidence a to various different values. Using the spectra detected by spectrum detector 313 and a mathematical model of the target structure, reconstruction calculations can be performed to arrive at measurement of CD and/or other parameters of interest. Alternatively or in addition, complementary higher diffraction orders detected by diffraction order detector 350 may be compared to determine asymmetry in the target structure, and therefore one or more related parameters of interest such as overlay, focus or dose, depending on the target properties.

Figure 6:
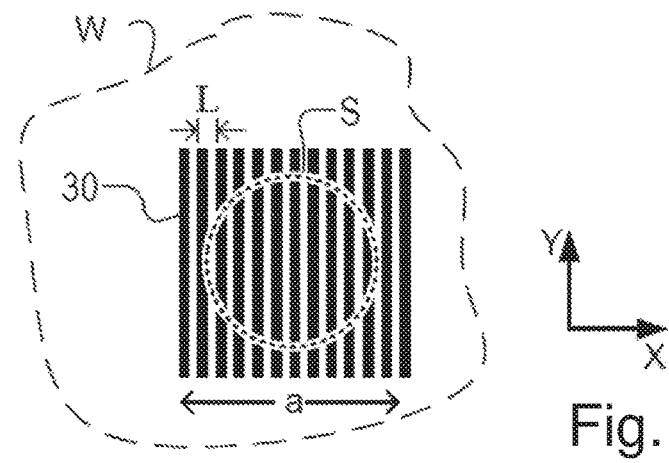
FIG. 6 illustrates the relationship between an illumination spot and a target grating in an example of the known scatterometers.

FIG. 6 illustrates a plan view of a typical substrate target 30, and the extent of illumination spot S in the scatterometer 200, 300 of FIG. 3 or FIG. 5. To obtain a diffraction spectrum that is free of interference from surrounding structures, the target 30 in the known method is a grating larger than the diameter of the illumination spot S. The diameter of spot S may be less than 2 μm and the grating width and length maybe be 5 μm. The substrate target 30 may be periodic with a pitch L. The grating in other words is 'underfilled' by the illumination, and the diffraction signal is free from interference by product features and the like outside the target grating itself. Referring specifically to the scatterometer 200 of FIG. 3 (although the principle is applicable to the scatterometer 300 of FIG. 5), the illumination arrangement comprising the illumination source 2, the lens system 12, the interference filter 13 and the polarizer 17 may be configured to provide illumination of a uniform intensity across a pupil plane of objective lens 15. Alternatively, by including an aperture in the illumination path, illumination may be restricted to on axis or off axis directions. As described in prior applications cited above, a modified scatterometer can use so-called dark field imaging to capture diffracted radiation from several smaller targets, all falling within the same illumination spot S.

Regardless of the type of inspection apparatus, it is generally required to position illumination spot S well enough in the center of target 30, or a false asymmetry may be generated that might be picked up as false overlay. The positioning budget consists of the stage positioning and also the size of the spot on the wafer (target). This size increases as with defocus. Therefore, disclosed herein is an improved focus control method for optimizing focus of the illumination spot S on the target 30. Also disclosed is an improved alignment method for aligning the illumination spot S on the target 30.

Illumination Spot Focus on Target

First of all, an optimized focus method will be described. If the spot S is not focused, then the illumination will fall on features other than the target 30, and the collected radiation will not allow an accurate measurement of the properties of the target 30. As mentioned already, focusing arrangements are known which pass a beam of radiation through the optical system and use some kind of detector system to obtain a signal representing focus error. For example, in published patent application US20080151228A, light reflected from the target is imaged onto two photodetectors with different focus offsets. Comparing the focused light intensity between the two photodetectors allows an indication of defocus of the optical system to be obtained, and the direction of defocus to be identified. The US patent application illustrates various simple photodetectors that may be used to obtain a measure of spot area. The contents of that patent application are incorporated herein by reference. Other types of focus arrangement can be envisaged, and the present disclosure is not limited to the technique of US 20080151228 A.

Disclosed is a method for monitoring a characteristic of illumination from a metrology apparatus to optimize focus. In an embodiment, the method comprises using the metrology apparatus to acquire an intensity measurement (e.g., from a pupil image) at different focus settings of the metrology apparatus. Each focus setting of the metrology apparatus corresponds to the metrology apparatus being used to attempt to focus the spot S at a different position in the Z-direction (i.e. the vertical direction). The Z-direction is perpendicular to the plane of the target 30.

In particular, each focus setting may correspond to a set defocus of the metrology apparatus. A defocus of zero corresponds to when the metrology apparatus is used to try to focus the spot S on the target 30 at the level of the target 30. Other focus settings corresponding to non-zero defocus values correspond to when the metrology apparatus is used to try to focus the spot S a certain distance (the defocus value) above or below the level of the target 30. It may be that the focus setting with a zero defocus value is the optimum focus setting of the metrology apparatus.

The metrology apparatus is used to inspect characteristics or properties of the substrate W. For example, the metrology apparatus can be used to measure the quality or accuracy of one or more patterns formed in layers of the substrate W. Accordingly, the characteristic of illumination from the metrology apparatus is monitored by acquiring pupil images on the target 30 of the substrate W that is to be inspected by the metrology apparatus. This is different from known techniques in which focus of a metrology apparatus may be calibrated using measurement of a fiducial that is part of the metrology apparatus. In particular, if the focus of the metrology apparatus is calibrated by making measurements of a fiducial of the metrology apparatus itself, then the results of this calibration do not take into account the different applications for which the metrology apparatus is to be used. For example, the calibration of the metrology apparatus does not take into account the properties of the substrate W which is to be inspected by the metrology apparatus.

Such a method of calibration may provide a sufficient level of accuracy for the focus of the metrology apparatus if the spot S formed by the metrology apparatus is intended to be sufficiently large and measures large targets (for example 40×40 μm). However, for newer generation metrology apparatuses, the metrology apparatus is designed to focus the illumination into a spot S having a smaller size and measure on smaller targets for example 4.5×4.5 μm targets. For example, in an embodiment each pupil image is formed by illuminating the target 30 with an illumination spot S having a diameter of at most 20 μm. In an embodiment, each pupil image is formed by illuminating the target 30 with an illumination spot S having a diameter of at most 10 μm, at most 5 μm, and optionally at most 2 μm. For example, according to specific examples, the metrology apparatus has an illumination spot S with a diameter of 1.9 μm, or 1.8 μm.

Calibrating the focus of the metrology apparatus using a fiducial of the metrology apparatus may not provide sufficient accuracy of the focus of the metrology apparatus. This may be a particularly severe problem for a metrology apparatus with a small illumination spot size, although the invention is not limited to use with a metrology apparatus having a small illumination spot size. The concepts described in this section can be used to improve the monitoring of a characteristic of illumination from a metrology apparatus having any spot size.

Figure 7A:
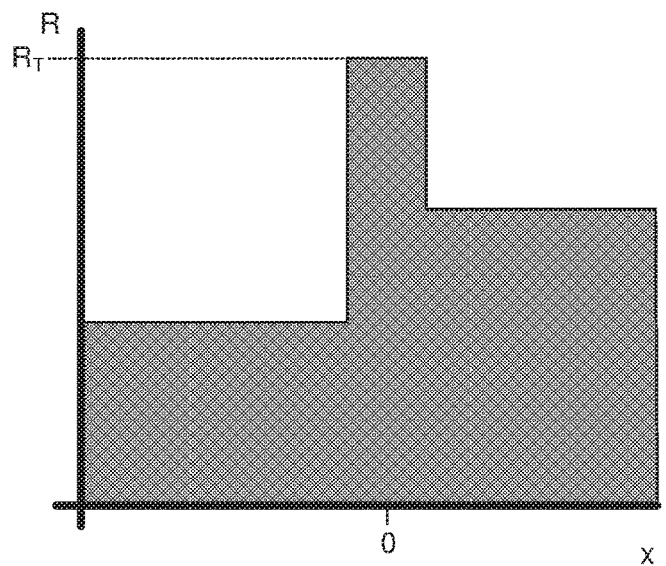
FIG. 7(a) shows a plot of reflectivity against position in the region of a target on a substrate.

Consider a target having some contrast (reflectivity difference) with its surroundings. If this substrate profile is measured with an (e.g., 2 μm FWHM) illumination spot, the total intensity in the pupil will essentially comprise a convolution of the spot intensity profile (which may comprise e.g., a Gaussian 2 μm FWHM profile, for example) and the reflectivity profile of the target and its surroundings. An example of such a reflectivity profile is shown in FIG. 7(a), which is a graph of reflectivity R (y-axis) of any order (e.g., zero order or any higher diffraction order) against substrate position x (x-axis) in the target region. The x=0 position is the target center, with the peak reflectivity ($R_T$) corresponding with the extent of the target area. Either side of the peak reflectivity area are areas of relatively lower reflectivity, the actual reflectivity being dependent on the structures (if any) located here.

Figure 7B:
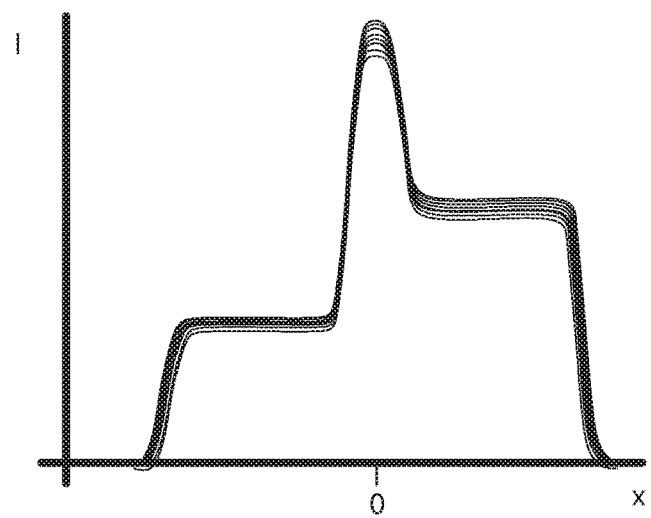
FIG. 7(b) shows a corresponding reflected intensity profile resultant from illumination of the same substrate region with an illumination spot.

FIG. 7(b) is a "total intensity pupil" plot of total intensity in the pupil plane against x for the same region of substrate as that of FIG. 7(a), and shows the deconvolution of the reflectivity profile of FIG. 7(a) and the Gaussian spot intensity profile (corresponding to the intensity profile of the illumination spot), for a number of different focus settings, with each plot (line) relating to a different focus setting.

When defocus is added, the size of the spot increases leading to a different result for the convolution. The total pupil intensity changes with defocus. This can be used to calibrate focus. In a first embodiment, measurements may be performed at a single location on the substrate. An alternative method may use measurements at multiple locations.

Figure 8:
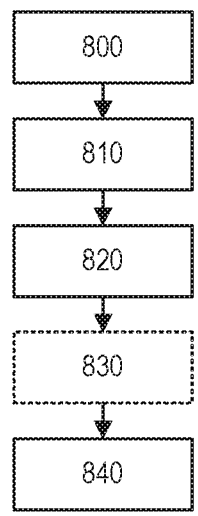
FIG. 8 is a flowchart of a focus optimization method according to an embodiment of the invention.

FIG. 8 is a flowchart of a method which comprising the following steps. At step 800, the illumination spot is positioned on the target at a first location (this step could use the alignment methods described later). The first location may be at the target center x=0, or alternatively at an off-center location (e.g., x=2 μm). At step 810, the total pupil intensity is measured for the first position. At step 820, the defocus level is changed and step 810 is repeated for a number of different defocus levels. At optional step 830, steps 810 and 820 are repeated for different positions on the target. At step 840, the optimal focus is determined. This may be correspond to the maximum (or alternatively minimum) intensity value (e.g., the (local) maximum or minimum of a curve of intensity against defocus). Where measurements have been made at different target locations (step 830), these additional measurements can be used to increase sensitivity of the determination at step 840. For example, the focus optimization may also use a determination of the width of the central (x=0) peak of the plot of FIG. 7(b); the optimal focus corresponding to the smallest illumination spot.

Figure 9:
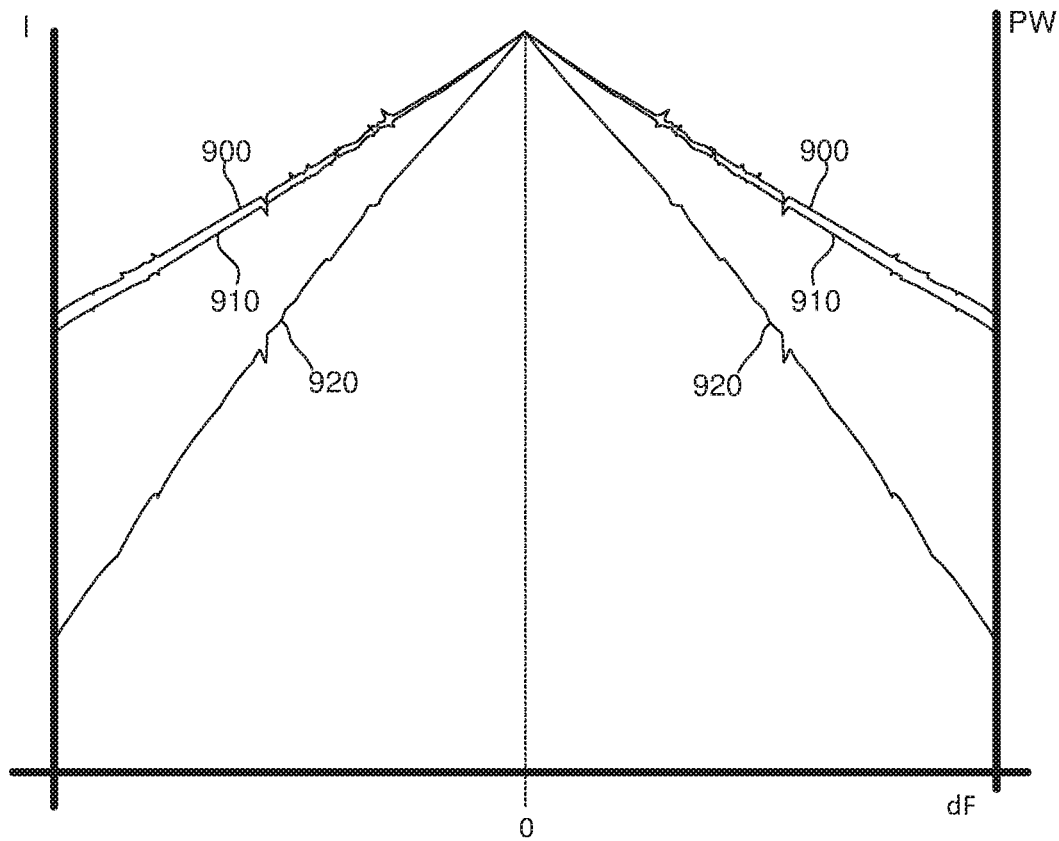
FIG. 9 is a is a graph illustrating the relationship between reflected intensity and pulse width against defocus.

FIG. 9 shows a plot of intensity I at the x=0 position 900 and a plot of intensity I at the x=2 μm position 910 against defocus dF. It can be seen that the intensity at both positions is at a maximum at the optimal focus (defocus=0). Also shown is a plot of peak width PW 920 of the central (x=0) peak of the plot of FIG. 7(b) against defocus dF. This peak width is also at a maximum at optimal focus (defocus=0). This can be observed from FIG. 7(b), where the uppermost plot corresponds to optimal focus, and, out of all the plots, has both maximum intensity over the extent of the target area and maximum peak width.

Although shown in one dimension (here specifically the x axis of FIGS. 7(a) and 7(b) show position in the x direction), it will be appreciated that the method may be performed for the two dimensions in the substrate plane (e.g., an intensity profile in the x/y plane).

In an embodiment, the determined focus setting is used for inspecting the substrate W throughout a die region adjacent to the target 30. For example, the target 30 may be positioned in the scribe lane adjacent to a die region of the substrate W. Once the target 30 has been used to calibrate the focus of the metrology apparatus, that calibrated focus setting may be used for the whole of that die region.

However, in an alternative embodiment, one target 30 is used to calibrate the focus of the metrology apparatus, and that calibrated focus setting may be used for a plurality of die regions of the substrate W. In a further alternative embodiment, an adjustment is made to the determined focus setting (determined from using one target 30) so as to estimate as focus setting having the best focus for a die region of the substrate W distanced from the target 30.

Hence, the user may have information about how the optimal focus setting of the metrology apparatus varies across the substrate W. This may be known based on information about the layer thicknesses throughout the substrate W for example. This information can be used to make an adjustment to the focus calibration of the metrology apparatus. Accordingly, based on the focus calibration from one target 30, an optimal focus of the metrology apparatus can be determined throughout the substrate W, even for die regions that are distanced from (i.e. not adjacent to) the target 30.

Illumination Spot Alignment onto Target

In addition to focus (z-direction), it is important that the illumination spot is properly aligned in the x/y plane onto the target. For a good measurement, a 3 µm diameter circular illumination spot is required to be positioned within a 4.5 µm square target. Alignment to within a +/−0.75 µm accuracy is challenging, particularly using an EUV metrology apparatus such as illustrated in FIG. 5, or an in-device metrology (IDM) tool. An IDM tool may comprise a scatterometer such as that illustrated in FIG. 3 which measures in pupil (e.g., using visible wavelengths) and is suitable for measuring in-device targets of 5×5 µm$^2$ or smaller (the illumination spot being 2 µm or similar). With an EUV metrology apparatus, there are a number of grazing incidence mirrors which direct the beam between illumination system 332 and target 30, between target 30 and diffraction grating 312, and between diffraction grating 312 and spectrum detector 313 (a path length of over 1 m). As a result, there are a number of pointing angle drifts and thermo-mechanical drifts in the optical path, as well as and wafer stage positioning drifts (e.g., as interferometers are not placed in vacuum and are therefore sensitive to temperature, pressure, and humidity drifts).

The alignment is preferably measured without any productivity penalty. This may be achieved by performing the alignment while stepping from one target to the next at nominal velocity, acceleration, and jerk. Furthermore, it is desired to sense the alignment error at an accuracy in the region of 50 nm using a direct measurement of the interaction between the measurement radiation and the target, in order to avoid introducing the mechanical complexity (due to limited volume), additional calibration effort, and the cost of an indirect measurement system.

In a proposed embodiment, the alignment method may exploit available metrology sensor outputs; in particular the diffraction order detector(s) 350 as shown in FIG. 5 and the wafer stage positioning sensor(s), e.g., interferometers. These sensor outputs may be used together with a model of the measurement radiation reflection on the target, and the exclusion zone around the target, to reconstruct the alignment error. The proposed alignment method has 3 steps:

1. Sensing: measure radiation intensity while moving towards, and away from, a target.
2. Metrology: reconstruct alignment error based on known motion and a reflection model.
3. Correction: adapt wafer stage motion set-point for next target (i.e., feed-forward).

Figure 10:
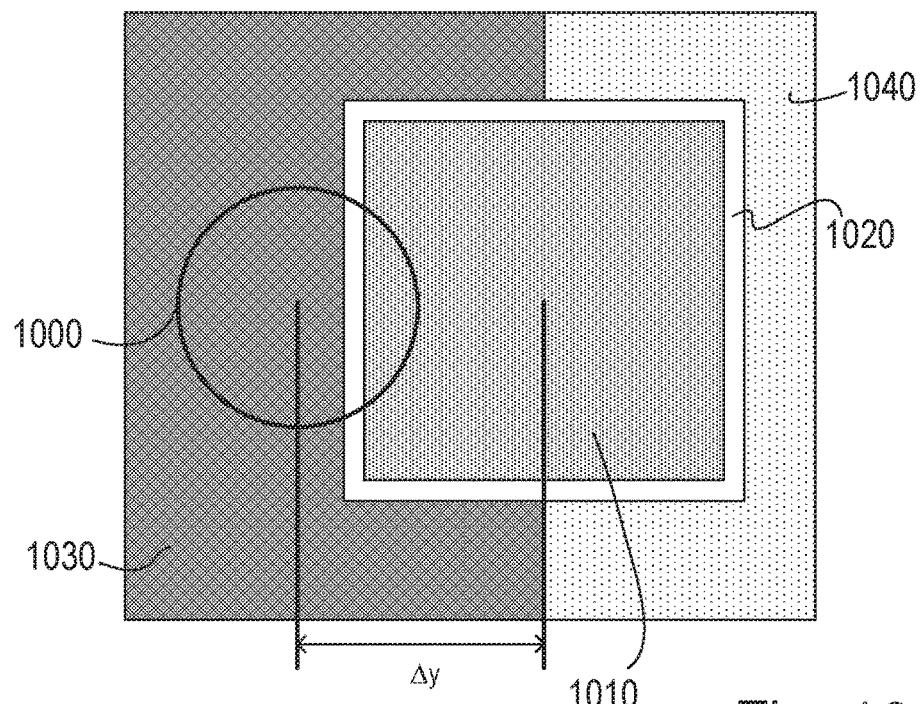
FIG. 10 is a schematic figure of a measurement illumination spot aligning onto a target.

FIG. 10 illustrates the alignment accuracy required. An approximately 3.0 µm circular illumination spot 1000 needs to be positioned within a square target 1010 having sides of length in the region of 4 µm-5 µm, e.g., 4.5 µm. The target has an exclusion zone 1020 in the region of 0.2 µm-0.3 µm, e.g., 0.25 µm, having a known structure, around its perimeter. The alignment error Δx, Δy is the distance between the center of illumination spot 1000 and the center of target 1010, and which is typically decomposed into an x component and a y component (only the alignment error Δy in the y direction is shown in the Figure). Also shown is the left (e.g., product) field 1030 and the right (e.g., product) field 1040.

Figure 11:
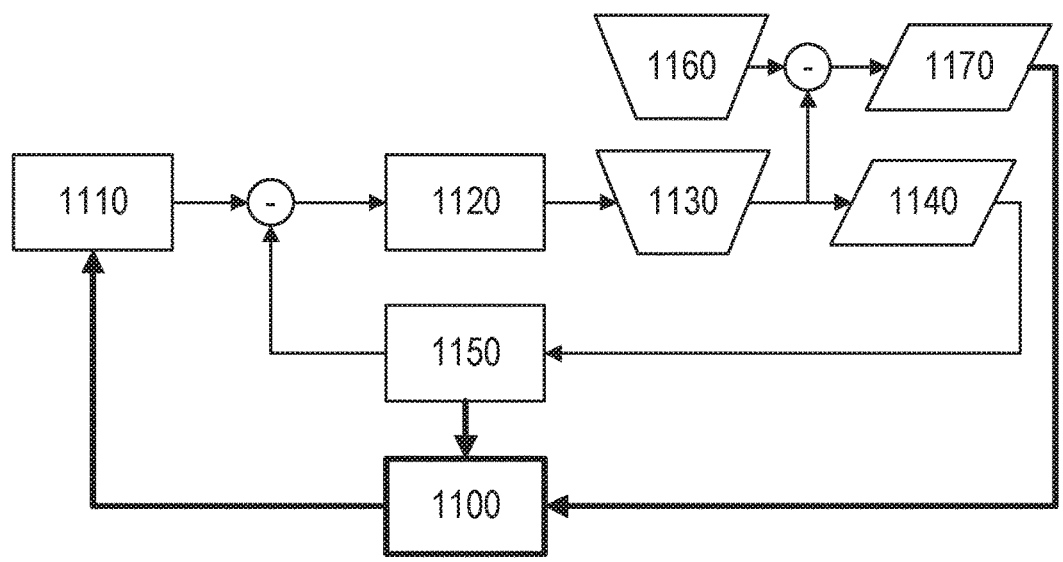
FIG. 11 is a flowchart of an alignment method according to an embodiment of the invention.

FIG. 11 is a block diagram of the proposed control loop, with the additional alignment reconstruction step 1100, and control paths highlighted in bold (the non-highlighted control steps/paths forming a present control arrangement). A set-point generator 1110 determines a positional set-point for the feedback controller 1120 of wafer stage positioning 1130. A stage sensor system, e.g., interferometers 1140 are used to perform metrology 1150 on targets to determine the actual stage position, and based on this metrology, a correction is determined for correcting the output of the set-point generator 1110. Also shown are the illumination source and optics positioning (e.g., measurement beam positioning) 1160 and a radiation detector, e.g., diffraction order detector 1170.

In the additional control loop disclosed herein, the diffraction order detector signal 1170 (e.g., measured light intensity of diffraction orders), along with the illumination source and optics positioning signal 1160 and wafer stage positioning signal 1130 (or alternatively the positional set-point if the resultant control error is acceptable), is used in the alignment reconstruction step 1100 to reconstruct the alignment error (e.g., using a reflection model). It is assumed that the main disturbances (or, drifts) are low-frequency, e.g., significantly less than 5 Hz. This is likely to be the case, at least in part, for several drift errors in the source, optical path, and wafer positioning. It is also envisaged that the computational reconstruction (step 1100) is possible within a timescale of approximately 30 ms, i.e., within a fraction of the step time between targets (which may be 60 ms). As an alternative, the correction may be applied one further target ahead so that the reconstruction time may take a full move-acquire time of 90 ms to 120 ms.

The sensors may be sampled at a high frequency of approximately 100 kHz for the diffraction order detector signal 1170 and of approximately 10 kHz for the wafer stage positioning 1130. The reconstruction may be performed once per target, hence updates at about 10 Hz (for a move-acquire time of 90 ms). The main stages of the alignment method described above will now be described in further detail.

Sensing: Measure First-Order Diffraction of Scattered Measurement Radiation on Target The diffraction order detector signal 1170, corresponding to the first diffraction orders from the target, is already used for overlay (OVL) or critical dimension (CD) metrology to measure geometric and/or optical parameters of the target. It is now proposed to use this detector 1170 for alignment. In an embodiment, diffraction order detector 1170 may be used for alignment during motion (e.g., immediately before and after the stage settles for a target measurement) and for OVL/CD (or other parameter) metrology during standstill, once settled.

Metrology: Reconstruct Alignment Error Based on Substrate Position and Reflection Model When the illumination spot is moving towards, or away from, a target, the diffracted radiation changes with the surface structure. This diffracted radiation may comprise any diffraction order and/or any other radiation form the target edges, exclusion zone and target surrounding which may scatter in the direction of the diffraction order detector even in the absence of any formal diffraction order. This scattered light will nonetheless give valuable information. Note that any discussion of the illumination spot moving to or from the target describes a relative movement of illumination spot and target, and may describe instances where is the illumination spot that actually moves, the wafer stage (and therefore target) that actually moves or where both the illumination spot and wafer stage moves. This diffracted reflection is expected to be different for the target, its exclusion zone, and the surrounding fields. The weight of the contribution of each surface structure depends on the surface integral of the intensity distribution of the illumination spot. Assuming that the diffraction of the target and the exclusion zone are known and sufficiently different, it is possible to recognize the transition from the exclusion zone to the target in the diffracted intensity, and to determine the alignment error from this and the known wafer stage position. This is illustrated in FIG. 12.

Figure 12A:
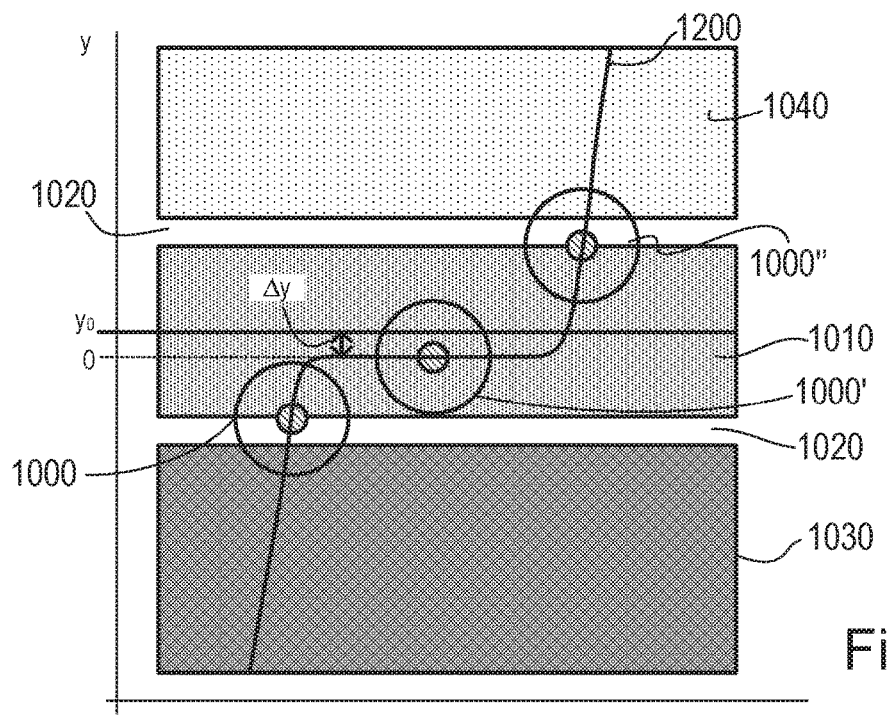
FIG. 12(a) shows a plot of position of an illumination spot with respect to a target on a substrate over time.
Figure 12B:
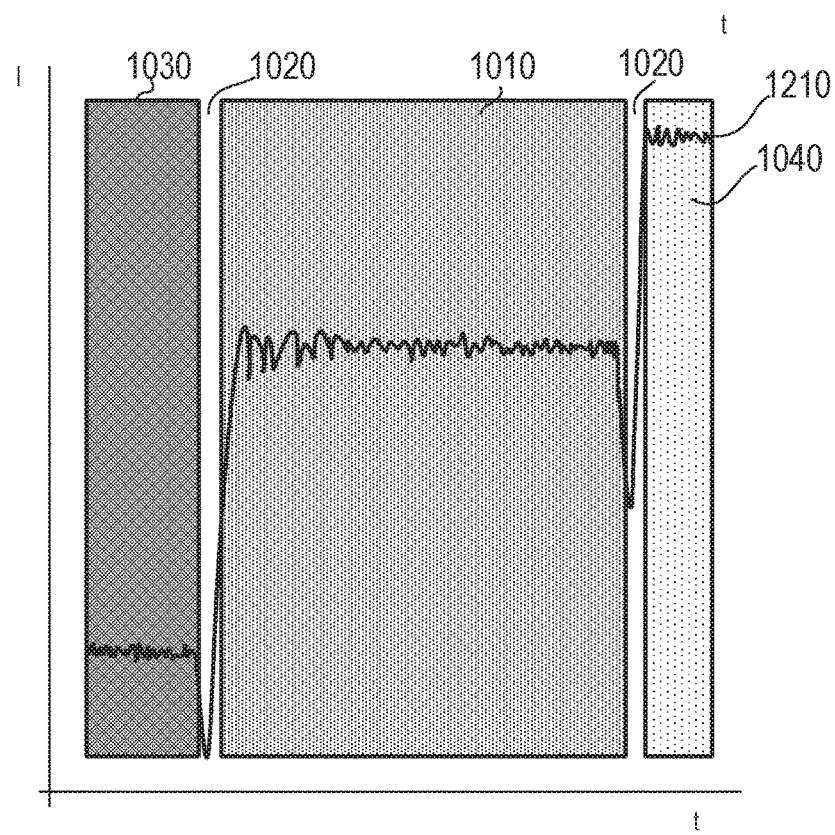
FIG. 12(b) shows a corresponding plot of the detected reflected intensity over the same time period.

FIG. 12(*a*) shows a plot of position (in y) against time. The shading and labelling correspond to that of FIG. 10. The Figure shows the path 1200 of the illumination spot against time t: 1) when the illumination spot 1000 first falls on target 1010 (i.e., immediately before it settles relative to the wafer stage), 2) when the illumination spot 1000' is at its settled, measurement position, and 3) immediately after the illumination spot 1000" has moved away from the target after acquisition. Also labelled on this graph is the settled position y=0 and the actual center of the target y=$y_0$. The difference between these positions is the alignment error $\Delta y$.

FIG. 12(*b*) shows the resultant intensity I signal 1210 measured on diffraction order detector 1170 against time t, over the same time period as that of FIG. 12(*a*). Once again, the shading and labelling correspond to that of FIG. 10. It can be seen from the signal 1210, that the transition from the exclusion zone to the target can be recognized, e.g., by a sharp dip in the signal intensity followed by a sharp rise as the target is encountered (when traveling to the target) or the next field is encountered (when traveling away from the target). Using this feature in combination with the known wafer stage position illustrated in FIG. 12(*a*), the alignment error $\Delta y$ can be reconstructed. In a first embodiment, a straightforward implementation comprises detecting a threshold violation (e.g., is the measured intensity above a threshold value indicative of the illumination spot being on the target) for the measured intensity on diffraction order detector 1170, while reading out the position sensor at that same time instant to derive the alignment error $\Delta y$. Although simple, such an approach may be insufficiently accurate, as it is sensitive to the shot noise of the detector (as it is based on only one sample) and (to a certain extent) to the unknown diffraction of the surrounding fields, whereas it requires a high sampling frequency (i.e., >300 kHz) to accurately define the edge.

Figure 13:
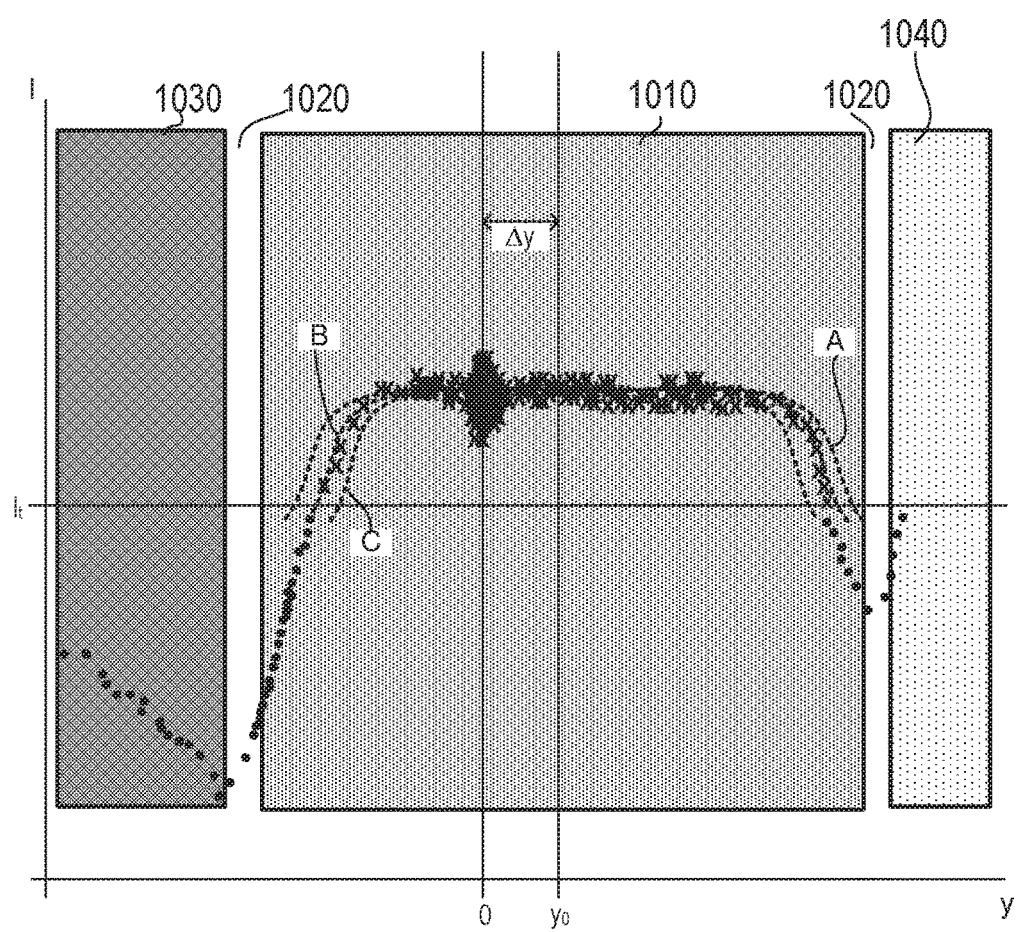
FIG. 13 is a plot of detected reflected intensity against substrate position illustrating an alignment error reconstruction method.

Therefore, in another embodiment, it is proposed to select a set of measurement points (e.g., based on a threshold condition) and to minimize the difference of a fit to this set of measurement points and a modelled curve based on the motion profile and a reflection model to reconstruct the alignment error. Such a method is illustrated in FIG. 13. The shading and labelling of substrate areas corresponds to the previous figures. FIG. 13 is a graph of intensity I against position y (or x). A threshold intensity level $I_t$ is labelled, as is the alignment error $\Delta y$, being the difference between the y=0 position (i.e., where the illumination spot settles relative to the wafer stage—as evidenced by the large number of samples at this position) and actual target center $y_0$. On the graph are measured intensity values against position. The dots are measured intensity values below the threshold intensity level $I_t$, which are not used in the reconstruction. The crosses are measured intensity values above the threshold intensity level $I_t$, which are the values used to reconstruct the alignment error. In an embodiment, the reflectivity of the exclusion zone may be specified in order to improve the signal (a large difference in reflectivity of the exclusion zone with respect to the target and with respect to the surrounding fields provides more variation in the signal, which makes it easier to separate from noise).

The method comprises using a diffraction model to obtain a modelled relationship between intensity and position as a function of the alignment error, and minimizing the difference between the modelled relationship and the observed relationship to reconstruct the alignment error. To conceptually illustrate this, three modelled plots A, B, C are shown, each corresponding to a different alignment error value $\Delta y$. It can also be seen that the modelled plot B best fits the observed data, and therefore the alignment error $\Delta y$ is that which corresponds to this modelled plot B. Performing a proper minimization (e.g. iteratively) may yield a more accurate result.

The above description relates to the y direction alignment error $\Delta y$. For each target, the alignment error should be reconstructed in the two directions of the substrate plane. In an embodiment, reconstruction of both the y direction alignment error $\Delta y$ and x direction alignment error $\Delta x$ is performed per-target. This may be done, for example, by controlling the illumination spot/wafer stage such that the illumination spot arrives on the target in the x direction and departs in the y direction (or vice versa). Alternatively, arrival and departure may be in the same direction for each acquisition and switched between targets. The latter option would increase the reconstruction accuracy as the fixed target size (up to nm-level) can be exploited and used in the reconstruction, and the number of measurement samples per reconstruction will be doubled.

In an embodiment, the diffraction model has no prior information on the diffraction of the surrounding fields. The above approach averages out noise and also includes samples in the reconstruction which are away from the edge/transition zones (e.g., nearer the target center) and therefore which are less influenced by the unknown surrounding fields. Moreover, it allows interpolation between data points and therefore enables a much lower and more realistic sampling frequency of 30-100 kHz. The solution of a least square optimization (not shown) is accurate within 50 nm (absolute mean+3 standard deviations) for 1000 random noise simulations. In this example, edge effects such as scattering are ignored. Depending on the impact, such effects may alternatively be included in the model, filtered away from the measurement, or even exploited as it may reveal even more useful information about the edge location.

Correction: Adapt Wafer Stage Control for Next Target

The reconstructed alignment error can be used to correct wafer stage control for a subsequent (e.g., the next) target, so as to minimize this alignment error for the subsequent target. Correction for the same target is also possible, but at a substantial productivity penalty. In an embodiment, the correction may be implemented by correcting the wafer stage motion set-point for the next target to be measured.

A number of refinements on the above concepts will now be described.

Source Power: Alignment Mode

A high source power is desirable to achieve a high signal-noise ratio, but the source power cannot be too high as the field surrounding the target can be damaged by the high dose. Source powers used for overlay metrology are too high for alignment. Therefore, in an embodiment, several illumination modes are proposed for the illumination source, which may include:

1. Off: when illumination spot is at away from the target by a significant distance, e.g., >5 µm;
2. Alignment mode: when illumination spot at smaller distance from the target, e.g., <5 µm, an optimized lower source power (relative to the acquisition mode below) for alignment may be used which avoids damaging the surrounding fields, and 3. Acquisition mode: when illumination spot is within target, an optimized high source power for (e.g., overlay or CD) metrology may be used.

Pixelated Detectors: Reflectivity Per Wavelength

The diffraction order detector 350 may comprise a pixelated photo detectors and, as such, contain spatial information regarding the scattered radiation. This spatial information can be used to distinguish the reflectivity per wavelength or scattering radiation which can be exploited to increase the reconstruction accuracy. In addition, the zeroth-order diffraction detector (labelled 313 in FIG. 5) can also be used to obtain more information.

Productivity: Acquire During Motion

Conventionally, a metrology acquisition begins at standstill after a dynamic settling period and finishes before the illumination spot moves to the next target. The time spent within the target without acquisition is approximately e.g., a few milliseconds for settling and e.g., a couple of milliseconds for deceleration and acceleration combined. The total move and settle period is significant with respect to the acquisition time and also with respect to the total move-acquire time. It is therefore proposed, in an embodiment, to avoid having a dedicated move and settle period, and instead use these e.g., few milliseconds for acquisition, thereby reducing the move-acquire time. This may comprise selecting images for which the illumination spot is within the target, out of the images sampled during the move and settle period and correcting for the alignment error (using the methods already described) for each of the selected images, before integration into a final image. More specifically, the method may comprise the following steps:

1. Begin acquisition a short time (e.g., a few ms) before arrival and finish acquisition a short time (e.g., a few ms) after departure, of the illumination spot at the aligned position;
2. Reconstruct the alignment error to determine (a posteriori) the dynamic alignment error, i.e., the alignment error for each image;
3. select the images for which the spot was within the target based on the dynamic alignment error; and
4. correct the positioning of each selected image based on the dynamic alignment error before integration into a final image.

Coarse Alignment

A coarse alignment is performed to locate the first target. A similar method as proposed above could be used to find the target, by scanning a certain area. A faster alternative is to use larger targets (e.g., 50-100 µm), which are already typically available in the scribe lane for lithographic purposes. The re-use of these targets avoids introducing dedicated targets for metrology, but requires an additional optical branch at a higher wavelength (e.g., visible) as the targets are not always in the top layer. For the relatively relaxed accuracy requirement of e.g., about 1 µm, the design can be relatively low-cost and compact based on state-of-the art optics, whereas an off-axis layout can address volume issues. A dedicated fiducial can be used to calibrate the distance between the axes (e.g., EUV and visible light).

Although specific reference may be made in this disclosure to the use of focus monitoring and control arrangements in inspection apparatuses such as scatterometers, it should be understood that the disclosed arrangements may have application in other types of functional apparatuses, as mentioned already above.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively.

Further embodiments according to the invention are described in below numbered clauses:

1. A method of optimizing within an inspection apparatus, the position and/or size of a measurement illumination spot relative to a target on a substrate, said method comprising:

detecting scattered radiation from at least the target resultant from illuminating the target, for different sizes and/or positions of said illumination spot relative to the target; and optimizing said position and/or size of the measurement illumination spot relative to the target based on a characteristic of the detected scattered radiation for the different sizes and/or positions of said illumination spot relative to the target.

2. A method according to clause 1, wherein the optimization step comprises optimizing the size of the measurement illumination spot relative to the target, the size of the measurement illumination spot being dependent upon focus of the measurement spot on the target, the method further comprising:

detecting said scattered radiation for different focus settings of the measurement illumination spot on the target; and selecting the optimal focus setting based on a comparison of the characteristic of the detected scattered radiation for each of the different focus settings.

3. A method according to clause 2, wherein the characteristic of the detected scattered radiation is intensity 4. A method according to clause 2 or 3, wherein the optimal focus setting corresponds to the highest or lowest value for said characteristic of the detected scattered radiation.

5. A method according to any of clauses 2 to 4, wherein said method further comprises performing said step of detecting said scattered radiation for different focus settings of the measurement illumination spot on the target, and also at different positions relative to the target, and selecting the optimal focus setting based on the characteristic of the detected scattered radiation from the different locations.

6. A method according to clause 5, further comprising determining a width of a peak in the relationship between the characteristic of the detected scattered radiation and position of the measurement illumination spot relative to the target for each of the different focus settings: and selecting the optimal focus setting based on a comparison of the width of said peaks for each of the different focus settings.

7. A method according to clause 1, wherein said detecting step comprises detecting scattered radiation from the target and its surroundings resultant from illuminating the target, for different positions of said illumination spot in the plane of the substrate, relative to the target; and said optimizing step comprises optimizing an aligned position of the measurement illumination spot relative to the target based on the characteristic of the detected scattered radiation for the different positions of said illumination spot relative to the target.

8. A method according to clause 7, wherein the characteristic of the detected scattered radiation is the intensity of the scattered radiation.

9. A method according to clause 8, wherein the intensity of the scattered radiation comprises the intensity of one or more detected non-zero diffraction orders.

10. A method according to any of clauses 7 to 9, wherein said detecting step comprises detecting scattered radiation from the target at different sampling instances in an acquisition time period during which the measurement illumination spot moves to the target, settles on the target and moves away from the target.

11. A method according to clause 10, wherein the aligned position is optimized for both orthogonal directions of the plane of the substrate in a single acquisition time period during which the direction that the illumination spot moves to the target and the direction that the illumination spot moves away from the target are mutually orthogonal.

12. A method according to clause 10, wherein the aligned position is optimized for each of the orthogonal directions of the plane of the substrate in separate acquisition time periods.

13. A method according to any of clauses 10 to 12, wherein further comprising:

reconstructing the alignment error for a plurality of images captured during said acquisition time period, said plurality of images including images captured when the measurement illumination spot is moving to the target and/or moving away from the target;

correcting the positioning of the measurement illumination spot on each image of the plurality of images; and integrating the plurality of images into a final image.

14. A method according to any of clauses 7 to 13, comprising detecting a position of the substrate and using the detected position of the substrate in said optimization step.

15. A method according to any of clauses 7 to 14, wherein said optimization step comprises reconstructing an alignment error, said alignment error being the difference in an actual aligned position and a desired aligned position.

16. A method according to clause 15, wherein said reconstruction of an alignment error comprises determining a profile of said characteristic of the detected scattered radiation with position relative to the target; and comparing the profile to a modeled profile which is dependent on alignment error.

17. A method according to clause 16, comprising reconstructing the alignment error by minimizing the difference between the modelled profile and the determined profile in terms of the alignment error.

18. A method according to clause 16 or 17, wherein the modeled profile is determined using a diffraction model of the illumination radiation, the target and an exclusion zone which at least partially surrounds the target.

19. A method according to any of clause 18, wherein said profile is determined using only values for a characteristic of the detected scattered radiation which exceed a threshold value.

20. A method according to 19, wherein said threshold value is based on an intensity level of diffraction from the target with respect to an intensity level of diffraction from the exclusion zone.

21. A method according to any of clauses 13 to 20, comprising determining a correction which minimizes the alignment error for positioning of a wafer stage holding the substrate in a measurement of a subsequent target.

22. A method according to any of clauses 7 to 21, comprising using spatial information in the detected scattered radiation to identify the diffraction from the target as a function of wavelength and to use this diffraction information in said optimization step.

23. A method according to any of clauses 7 to 22, wherein said measurement illumination spot is sourced from an illumination source which is operable in an alignment mode in which the source power is lower than in an acquisition mode during which a parameter of the target is measured.

24. A method according to clause 23, wherein said illumination source is switched to an off state during a time interval when said illumination spot is at least one spot diameter distant from the target.

25. A method according to any preceding clause wherein the illumination source is a high harmonic generation source operable to produce radiation in the 1 to 100 nm wavelength range.

26. A metrology apparatus for measuring a parameter of a lithographic process, the metrology apparatus being operable to perform the method of any of clauses 1 to 25.

27. A non-transitory computer program product comprising machine-readable instructions for causing a processor to cause performance of the method of any of clauses 1 to 25.

28. A system comprising:

an inspection apparatus configured to provide a radiation beam on a target on a substrate and to detect radiation diffracted by the target to determine a parameter of a patterning process; and the non-transitory computer program product of clause 27.

29. The system of clause 28 comprising a high harmonic generation source operable to produce said radiation beam, wherein said radiation beam comprises radiation in the 1 to 100 nm wavelength range.

30. The system of clause 28 or 29, further comprising a lithographic apparatus comprising a support structure configured to hold a patterning device to modulate a radiation beam and a projection system arranged to project the modulated radiation beam onto a radiation-sensitive substrate.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of optimizing, within an inspection apparatus, a position and/or size of a measurement illumination spot relative to a target on a substrate, the method comprising:

detecting a characteristic of scattered radiation from at least the target and surroundings of the target, resultant from illuminating the target, for different sizes and/or positions of the illumination spot relative to the target; and optimizing the position and/or size of the measurement illumination spot relative to the target based on the detecting, wherein the optimizing comprises optimizing an aligned position of the measurement illumination spot relative to the target based on the characteristic.

2. The method of claim 1, wherein:

the size of the measurement illumination spot is dependent upon a focus of the measurement illumination spot on the target; and the method further comprises selecting an optimal focus setting based on a comparison of the characteristic for different focus settings.

3. The method of claim 2, wherein the optimal focus setting corresponds to a highest or a lowest value of the characteristic.

4. The method of claim 2, wherein:

the different positions relative to the target correspond to positions on a surface of the substrate; and the selecting is further based on the characteristic as detected from the positions on the surface of the substrate.

5. The method of claim 4, further comprising:

determining a width of a peak in a relationship between the characteristic and the positions on the surface of the substrate for each of the different focus settings; and selecting the optimal focus setting based on a comparison of the width of the peak for each of the different focus settings.

6. The method of claim 1, wherein the characteristic is an intensity of the scattered radiation.

7. The method of claim 1, wherein the characteristic comprises one or more non-zero diffraction orders of the scattered radiation.

8. The method of claim 1, wherein the detecting comprises detecting the scattered radiation at different sampling instances in an acquisition time period during which the measurement illumination spot moves to the target, settles on the target and moves away from the target.

9. The method of claim 8, wherein the aligned position is optimized for both orthogonal directions of a plane of the substrate in a single acquisition time period during which a direction that the illumination spot moves to the target and the direction that the illumination spot moves away from the target are mutually orthogonal.

10. The method of claim 8, wherein the aligned position is optimized for each of the orthogonal directions of a plane of the substrate in separate acquisition time periods.

11. The method of claim 8, further comprising:

reconstructing an alignment error for a plurality of images captured during the acquisition time period, wherein the plurality of images comprises images captured when the measurement illumination spot is moving to the target and/or moving away from the target;

correcting a positioning of the measurement illumination spot on each image of the plurality of images based on the alignment error; and integrating the plurality of images into a final image.

12. The method of claim 1, further comprising detecting a position of the substrate, wherein the optimizing the position and/or size of the measurement illumination spot relative to the target is further based on the position of the substrate.

13. The method of claim 1, further comprising reconstructing an alignment error of the measurement illumination spot, the alignment error comprising a difference between an actual aligned position and a desired aligned position.

* * * * *